US009592272B2

(12) United States Patent
Berenbaum et al.

(10) Patent No.: US 9,592,272 B2
(45) Date of Patent: Mar. 14, 2017

(54) TREATMENT OF OSTEOARTHRITIS WITH INCRETIN HORMONES OR ANALOGUES THEREOF

(71) Applicants: UNIVERSITE PIERRE ET MARIE CURIE (PARIS 6), Paris (FR); ASSISTANCE PUBLIQUE—HOPITAUX DE PARIS, Paris (FR)

(72) Inventors: Francis Berenbaum, Gif sur Yvette (FR); Carole Bougault, Lyons (FR); Claire Attali, Antony (FR)

(73) Assignees: UNIVERSITE PIERRE ET MARIE CURIE (PARIS 6), Paris (FR); ASSISTANCE PUBLIQUE—HÔPITAUX DE PARIS, Paris (FR)

( * ) Notice: Subject to any disclaimer, the term of this patent is extended or adjusted under 35 U.S.C. 154(b) by 0 days.

(21) Appl. No.: 14/424,475

(22) PCT Filed: Aug. 29, 2013

(86) PCT No.: PCT/FR2013/051998
§ 371 (c)(1),
(2) Date: Feb. 27, 2015

(87) PCT Pub. No.: WO2014/023923
PCT Pub. Date: Feb. 13, 2014

(65) Prior Publication Data
US 2015/0209411 A1 Jul. 30, 2015

(30) Foreign Application Priority Data
Aug. 30, 2012 (FR) .................................. 12 58100

(51) Int. Cl.
*A61K 38/22* (2006.01)
*A61K 38/26* (2006.01)
*A61K 45/06* (2006.01)

(52) U.S. Cl.
CPC .............. *A61K 38/22* (2013.01); *A61K 38/26* (2013.01); *A61K 45/06* (2013.01)

(58) Field of Classification Search
CPC .............................. C07K 14/605; A61K 38/26
See application file for complete search history.

(56) References Cited

FOREIGN PATENT DOCUMENTS

WO   WO 2012/100748   * 8/2012

OTHER PUBLICATIONS

English machine translation from Google translate of WO 2012/100748 downloaded Jan. 29, 2016.*
"Combining a GLP-1 Agonist and a DPP-4 Inhibitor for Type 2 Diabetes" Pharmacist's Letter / Prescriber's Letter Aug. 2012, 3 pages.*
"FDA Drug Safety Communication: FDA warns that DPP4 inhibitors for type 2 diabetes may cause severe joint pain," published Aug. 28, 2015, dowloaded from fda.gov on Jan. 29, 2016, 4 pages.*
"Osteoarthritis Symptoms" dowloaded from mayoclinic.org on Jan. 29, 2016, 7 pages.*
Altman & Barthel "Topical therapies for osteoarthritis" Drugs. Jul. 9, 2011;71(10):1259-79.*
Goodwin et al. "Intra-articular steroid injections for painful knees," Can Fam Physician. Feb. 2004; 50: 241-248.*
Dicembrini, I. et al. "Bone: Incretin Hormones Perceiver or Receiver?" *Experimental Diabetes Research*, Jun. 17, 2012, pp. 1-5, vol. 2012.
Ding, K.-H. et al. "Impact of Glucose-Dependent Insulinotropic Peptide on Age-Induced Bone Loss" *Journal of Bone and Mineral Research*, Apr. 2008, pp. 536-543, vol. 23, No. 4.
Vittone, F. et al. "Sitagliptin reduces plaque macrophage content and stabilises arteriosclerotic lesions in Apoe$^{-/-}$ mice" *Diabetologia*, May 18, 2012, pp. 2267-2275, vol. 55, No. 8.
Chen, T.-H. et al. "Exendin-4 attenuates lipopolysaccharides induced inflammatory response but does not protects H9c2 cells from apoptosis" *Immunopharmacology and Immunotoxicology*, Jun. 2012, pp. 484-490, vol. 34, No. 3.

* cited by examiner

*Primary Examiner* — Christina Bradley
(74) *Attorney, Agent, or Firm* — Saliwanchik, Lloyd & Eisenschenk

(57) ABSTRACT

The present invention relates to the use of the incretin hormones glucagon-like peptide-1 or GLP-1 and glucose-dependent insulinotropic polypeptide or GIP, or of analogs thereof, in particular the analogs resistant to dipeptidyl peptidase IV, in the treatment of osteoarthritis, in particular for inhibiting or slowing down cartilage destruction.

14 Claims, 4 Drawing Sheets

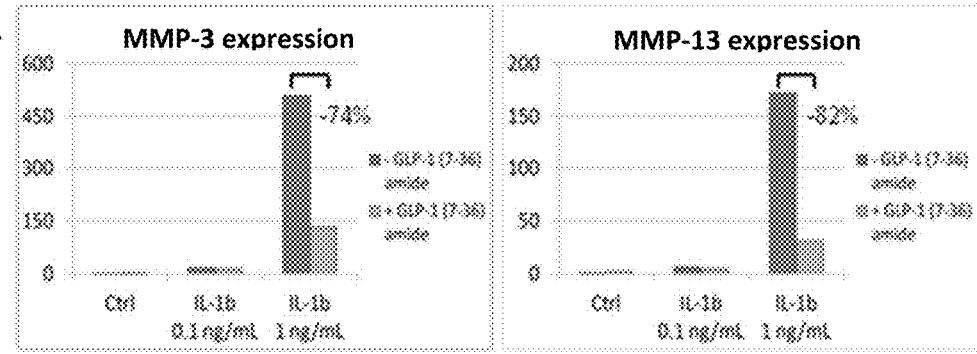
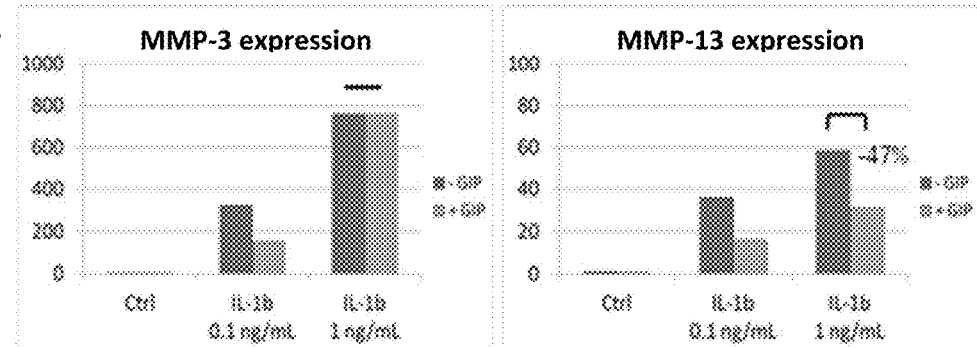
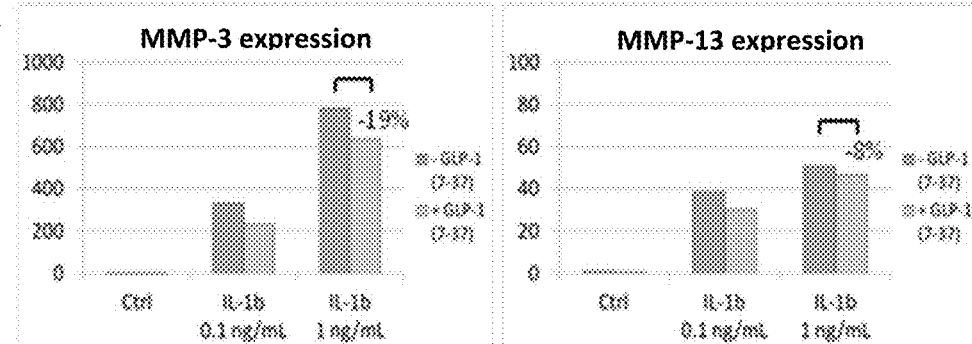

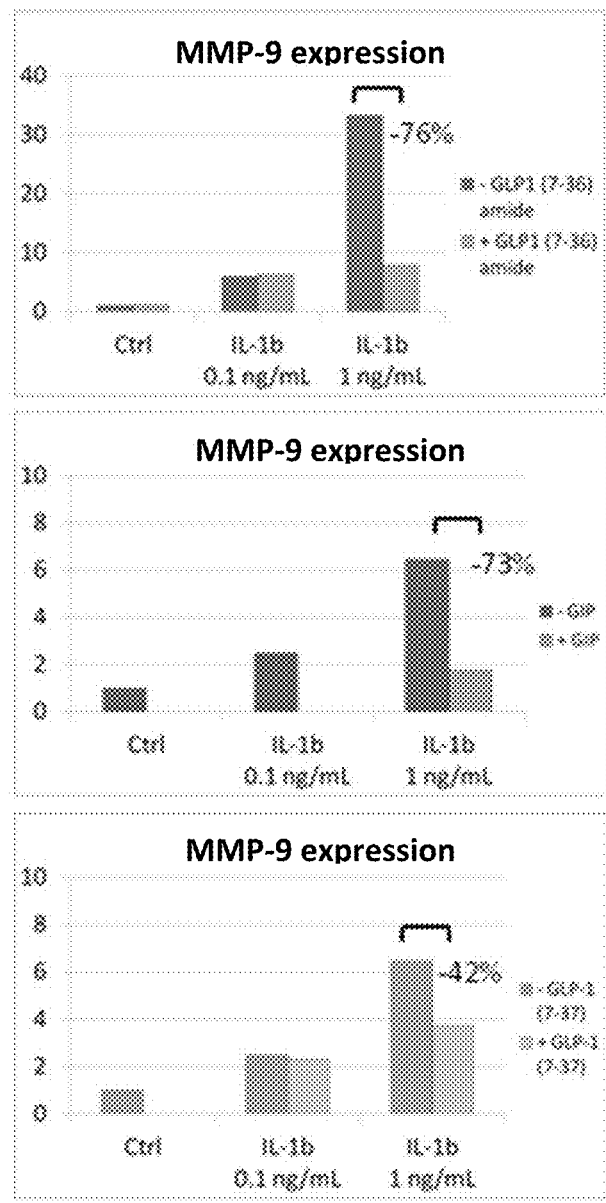

SEQUENCE LISTING

<160> NUMBER OF SEQ ID NOS: 16

<210> SEQ ID NO 1
<211> LENGTH: 180
<212> TYPE: PRT
<213> ORGANISM: Homo sapiens

<400> SEQUENCE: 1

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys

```
            50                  55                  60
Tyr Leu Asp Ser Arg Arg Ala Gln Asp Phe Val Gln Trp Leu Met Asn
 65                  70                  75                  80

Thr Lys Arg Asn Arg Asn Ile Ala Lys Arg His Asp Glu Phe Glu
                 85                  90                  95

Arg His Ala Glu Gly Thr Phe Thr Ser Asp Val Ser Ser Tyr Leu Glu
                100                 105                 110

Gly Gln Ala Ala Lys Glu Phe Ile Ala Trp Leu Val Lys Gly Arg Gly
            115                 120                 125

Arg Arg Asp Phe Pro Glu Glu Val Ala Ile Val Glu Glu Leu Gly Arg
        130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 2
<211> LENGTH: 37
<212> TYPE: PRT
<213> ORGANISM: Homo sapiens

<400> SEQUENCE: 2

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
                20                  25                  30

Val Lys Gly Arg Gly
            35

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
                20                  25                  30

<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
                20                  25                  30

<210> SEQ ID NO 5
<211> LENGTH: 153
<212> TYPE: PRT
<213> ORGANISM: Homo sapiens

<400> SEQUENCE: 5
```

```
Met Val Ala Thr Lys Thr Phe Ala Leu Leu Leu Ser Leu Phe Leu
1               5                   10                  15

Ala Val Gly Leu Gly Glu Lys Lys Glu Gly His Phe Ser Ala Leu Pro
            20                  25                  30

Ser Leu Pro Val Gly Ser His Ala Lys Val Ser Ser Pro Gln Pro Arg
            35                  40                  45

Gly Pro Arg Tyr Ala Glu Gly Thr Phe Ile Ser Asp Tyr Ser Ile Ala
            50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Glu Ala
            100                 105                 110

Val Glu Pro Gln Ser Ser Pro Ala Lys Asn Pro Ser Asp Glu Asp Leu
            115                 120                 125

Leu Arg Asp Leu Leu Ile Gln Glu Leu Leu Ala Cys Leu Leu Asp Gln
            130                 135                 140

Thr Asn Leu Cys Arg Leu Arg Ser Arg
145                 150

<210> SEQ ID NO 6
<211> LENGTH: 42
<212> TYPE: PRT
<213> ORGANISM: Homo sapiens

<400> SEQUENCE: 6

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 7
<211> LENGTH: 23
<212> TYPE: DNA
<213> ORGANISM: Artificial
<220> FEATURE:
<223> OTHER INFORMATION: HPRT antisense primer

<400> SEQUENCE: 7
attcaaatcc ctgaagtact cat                                        23

<210> SEQ ID NO 8
<211> LENGTH: 17
<212> TYPE: DNA
<213> ORGANISM: Artificial
<220> FEATURE:
<223> OTHER INFORMATION: HPRT sense primer

<400> SEQUENCE: 8
aggacctctc gaagtgt                                               17

<210> SEQ ID NO 9
<211> LENGTH: 20
<212> TYPE: DNA
<213> ORGANISM: Artificial
<220> FEATURE:
<223> OTHER INFORMATION: GLP1R antisense primer
```

```
<400> SEQUENCE: 9
cagtcggcag cctagagagt                                                   20

<210> SEQ ID NO 10
<211> LENGTH: 18
<212> TYPE: DNA
<213> ORGANISM: Artificial
<220> FEATURE:
<223> OTHER INFORMATION: GLP1R sense primer

<400> SEQUENCE: 10
ctgcccagca acaccagt                                                     18

<210> SEQ ID NO 11
<211> LENGTH: 21
<212> TYPE: DNA
<213> ORGANISM: Artificial
<220> FEATURE:
<223> OTHER INFORMATION: MMP-3 sense primer

<400> SEQUENCE: 11
tgaaaatgaa gggtcttccg g                                                 21

<210> SEQ ID NO 12
<211> LENGTH: 20
<212> TYPE: DNA
<213> ORGANISM: Artificial
<220> FEATURE:
<223> OTHER INFORMATION: MMP-3 antisense primer

<400> SEQUENCE: 12
gcagaagctc cataccagca                                                   20

<210> SEQ ID NO 13
<211> LENGTH: 19
<212> TYPE: DNA
<213> ORGANISM: Artificial
<220> FEATURE:
<223> OTHER INFORMATION: MMP-9 sense primer

<400> SEQUENCE: 13
aactacggtc gcgtccact                                                    19

<210> SEQ ID NO 14
<211> LENGTH: 20
<212> TYPE: DNA
<213> ORGANISM: Artificial
<220> FEATURE:
<223> OTHER INFORMATION: MMP-9 antisense primer

<400> SEQUENCE: 14
ccacagccaa ctatgaccag                                                   20

<210> SEQ ID NO 15
<211> LENGTH: 21
<212> TYPE: DNA
<213> ORGANISM: Artificial
<220> FEATURE:
<223> OTHER INFORMATION: MMP-13 sense primer

<400> SEQUENCE: 15
tgatggcact gctgacatca t                                                 21

<210> SEQ ID NO 16
<211> LENGTH: 20
```

```
<212> TYPE: DNA
<213> ORGANISM: Artificial
<220> FEATURE:
<223> OTHER INFORMATION: MMP-13 antisense primer

<400> SEQUENCE: 16 tgtagcctttt ggaactgctt                                                    20
```

TREATMENT OF OSTEOARTHRITIS WITH INCRETIN HORMONES OR ANALOGUES THEREOF

CROSS-REFERENCE TO RELATED APPLICATION

This application is the U.S. national stage application of International Patent Application No. PCT/FR2013/051998, filed Aug. 29, 2013.

The Sequence Listing for this application is labeled "Seq-List.txt" which was created on Feb. 25, 2015 and is 7 KB. The entire content of the sequence listing is incorporated herein by reference in its entirety.

The present invention relates to the field of medicine, and more particularly to that of the treatment of osteoarthritis.

TECHNOLOGICAL BACKGROUND OF THE INVENTION

Osteoarthritis or degenerative chronic arthropathy is a chronic joint disease characterized by structural deterioration of joint cartilage. The symptoms of this pathological condition can vary depending on the joint concerned, but are generally characterized by persistent pain associated with a functional impairment, i.e., a limitation of the mobility of the joint concerned.

Joint cartilage is a connective tissue composed of chondrocytes and an extracellular matrix essentially formed from water, proteoglycans and collagen. Chondrocytes have a fundamental role in the homeostasis of the extracellular matrix in which they ensure its synthesis and renewal. The maintaining of cartilage therefore depends on continuous complex exchanges between the chondrocytes and the matrix and is continually subjected to a critical equilibrium between the degradation mechanisms, under the influence of destructive cytokines, in particular the pro-inflammatory cytokines TNF-α and IL-1β, and the synthesis or restoring mechanisms under the effect of modulating cytokines and growth factors, in particular IGF-1, TGF-β, and certain BMPs (bone morphogenetic proteins).

The arthrotic destruction of cartilage is the result of an imbalance between the anabolic and catabolic mechanisms of the extracellular matrix. Several factors can promote rupturing of the homeostasis of the matrix, in particular mechanical factors associated, for example, with joint overload in an obese patient, trauma, repeated microtraumas or architectural defects of the joint, metabolic, genetic or hormonal factors, or aging. However, the initiation of the arthrotic process still remains very poorly understood at the current time.

The imbalance between the anabolic and catabolic mechanisms essentially results in an increase in the synthesis of metalloproteases (MMPs) (Blanc et al., 1999), a decrease in the synthesis of TIMPs (tissue inhibitors of metalloproteinases, the physiological inhibitors of MMPs) and an inhibition of matrix constituent synthesis by chondrocytes. This imbalance is accentuated by an accelerated chondrocyte apoptosis phenomenon (Hashimoto et al., 1998) and by chondrocyte activation via various mediators released by the synovial tissue (Sellam and Berenbaum, 2010). The pro-inflammatory cytokine IL-1β synthesized by chondrocytes and synoviocytes has a major role in this arthrotic destruction process. It induces not only an increase in MMP production by chondrocytes, but also a reduction of the anabolic capacities and the apoptosis of these cells (Goldring et al., 2008). Furthermore, the subchondral bone also participates in matrix-degrading phenomena, in particular by means of the secretion of proteolytic enzymes by osteoblasts (Sanchez et al., 2012).

The matrix metalloproteases (MMPs) involved in the matrix proteolysis of osteoarthritis are collagenases, stromelysins, gelatinases and membrane metalloproteases (Rannou et al., 2005). Not all of these enzymes are specific for cartilage, and they are involved in numerous physiological processes, in particular the remodeling of numerous connective tissues (Nagase et al., 1999). The interstitial collagenases (MMP-1, -8, and -13) are capable of degrading collagens I, II, III, IV and VII. The collagen thus denatured by these enzymes becomes a substrate for gelatinases. The stromelysins (MMP-3, -10, and -11) are capable of degrading proteoglycans, gelatin, fibronectin and collagen type IX, but only MMP-3 appears to be involved in the degradation of the cartilaginous matrix (Stove et al., 2001). The gelatinases (MMP-2 and -9) degrade denatured interstitial collagen and collagens IV and V. In addition, it has been demonstrated that MMP-1, -3 and -13 are also capable of degrading proteoglycans (Little et al., 2002). Other enzymes, in particular the aggrecanases ADAMTS-4 and -5, are also thought to play a role in matrix proteolysis (Fosang and Little, 2008).

In addition to metalloproteases, other catabolic mediators participate in arthrotic degeneration, in particular prostaglandin E2 (PGE2), which is involved in cartilage degradation and chondrocyte apoptosis (Hardy et al., 2002; Miwa et al., 2000).

The treatments proposed for patients suffering from osteoarthritis are symptomatic since, at the current time, there is no curative treatment for this pathological condition. The drug treatments are symptomatic treatments with an immediate action (analgesics, non-steroidal anti-inflammatories) or with a delayed action (for example, drugs comprising chondroitin sulphate (Structum, Chondrosulf), diacerein (Art 50, Zondar), unsaponifiable extracts of avocado and of soya (Piascledine) or hyaluronic acid.

Because of their key role in cartilage destruction, metalloproteases have become favoured targets in the search for new compounds capable of slowing down or stopping the progression of osteoarthritis. However, these proteins are involved in numerous physiological processes and inhibiting them may produce unforeseeable side effects. That was, for example, the case with the compound PG-116800, the musculoskeletal toxicity of which was revealed during clinical trials (Krzeski et al., 2007).

Currently, osteoarthritis is thought to affect approximately nine to ten million individuals in France, including 4.6 million with symptomatic osteoarthritis. Given the aging of the population and also the increase in the prevalence of obesity in developed countries, a very large increase in the number of arthrotic patients is expected in the coming years. This increase will be extremely expensive, not only in terms of quality of life, but also from an economic point of view for treating the patients. It therefore remains essential to rapidly develop new strategies for inhibiting or slowing down cartilage destruction in individuals suffering from osteoarthritis.

SUMMARY OF THE INVENTION

The objective of the present invention is to provide new compounds which can be used in the treatment of osteoarthritis.

The inventors have demonstrated that the incretin hormones GLP-1 (glucagon-like peptide 1) and GIP (gastric inhibitory peptide or glucose-dependent insulinotropic polypeptide) are capable of inhibiting the overexpression of several metalloproteases (MMP-3, MMP-13 and MMP-9) and of prostaglandin E2 (PGE2) in osteoblasts and chondrocytes in response to the pro-inflammatory cytokine IL-1β. They have thus shown that incretin hormones are capable of blocking the overexpression of several prodegradative mediators involved in the arthrotic destruction process.

Thus, the present invention relates to an incretin hormone or an analogue thereof for use in the treatment of osteoarthritis. More particularly, the invention relates to a peptide selected from the group consisting of the GLP-1 peptide, the GIP peptide and analogues of said peptides resistant to dipeptidyl peptidase IV (DPP-IV) for use in the treatment of osteoarthritis.

The peptide used according to the invention may in particular comprise a sequence selected from the group consisting of the sequences SEQ ID NO: 1 to 6.

In particular, the peptide may be selected from the group consisting of the GLP-1 (7-36) amide peptide (SEQ ID NO: 4), the GLP-1 (7-37) peptide (SEQ ID NO: 3) and the GIP (1-42) peptide (SEQ ID NO: 6). Preferably, the peptide is selected from the group consisting of the GLP-1 (7-36) amide peptide (SEQ ID NO: 4) and the GLP-1 (7-37) peptide (SEQ ID NO: 3).

The peptide may also be an analogue of the GLP-1 or GIP peptide resistant to DPP-IV. Preferably, the peptide is an analogue of the GLP-1 peptide resistant to DPP-IV, in particular an analogue selected from the group consisting of exenatide, liraglutide, exendin-4, albiglutide, taspoglutide, lixisenatide, LY315902, dulaglutide (LY2189265), LY2199265, LY2428757, semaglutide (NN9535), CJC-1131, CJC-1134 and ZP10. The peptide may also be an analogue selected from the group consisting of exenatide, liraglutide, exendin-4, albiglutide, taspoglutide, lixisenatide, LY315902, LY2199265, LY2428757, NN9535, CJC-1131, CJC-1134 and ZP10. Quite particularly preferably, the peptide is an analogue selected from the group consisting of exenatide and liraglutide.

The peptide used according to the invention can be used in the treatment of osteoarthritis in combination with one or more other active substances. In this case, the peptide and the other active substance(s) are administered simultaneously or sequentially.

The peptide used according to the invention may in particular be used in combination with inhibitors of the dipeptidyl peptidase IV enzyme, preferably selected from the group consisting of sitagliptin, saxagliptin, vildagliptin, alogliptin and linagliptin, or other substances such as analgesics, non-steroidal anti-inflammatories, steroidal anti-inflammatories and slow-acting anti-arthritic agents. The peptide may also be administered in combination with local treatments for osteoarthritis.

The peptide used according to the invention may be administered in its mature form, in the form of a precursor or in the form of a nucleic acid encoding said peptide.

Preferably, the peptide used according to the invention is intended to be administered orally, subcutaneously, intravenously or intra-articularly.

The present invention also relates to a pharmaceutical composition comprising one or more peptides as used according to the invention, and one or more pharmaceutically acceptable supports and/or excipients, for use in the treatment of osteoarthritis.

The present invention also relates or a pharmaceutical composition comprising one or more peptides as used according to the invention, or one or more nucleic acids encoding one or more peptides as used according to the invention, and one or more pharmaceutically acceptable supports and/or excipients, for use in the treatment of osteoarthritis.

The composition may also comprise one or more other active substances, in particular one or more inhibitors of the dipeptidyl peptidase IV enzyme, preferably selected from the group consisting of sitagliptin, saxagliptin, vildagliptin, alogliptin and linagliptin, or other active substances such as analgesics, non-steroidal anti-inflammatories, steroidal anti-inflammatories and slow-acting anti-arthritic agents.

The composition may be formulated in the form of an ingestible or injectable composition, preferably in the form of a composition intended to be administered orally, subcutaneously, intravenously or intra-articularly.

BRIEF DESCRIPTION OF THE DRAWINGS

FIG. 1: Effect of the GLP-1 (7-36) amide, GLP-1 (7-37) or GIP peptide on the induction of the expression of the MMP-3, MMP-9 and MMP-13 enzymes in chondrocytes in response to IL-1β (0.1 ng/ml or 1 ng/ml). The values obtained by real-time quantitative RT-PCR are standardized with respect to the values obtained with the control (without IL-1β and without GLP-1 or GIP). A: MMP-3 and MMP-13 expression in the presence or absence of GLP-1 (7-36) amide (10 nM); B: MMP-3 and MMP-13 expression in the presence or absence of GIP (10 nM); C: MMP-3 and MMP-13 expression in the presence or absence of GLP-1 (7-37) (10 nM); D: MMP-9 expression in the presence or absence of GLP-1 (7-36) amide (10 nM), GLP-1 (7-37) (10 nM) or GIP (10 nM).

DETAILED DESCRIPTION OF THE INVENTION

Figure 2:
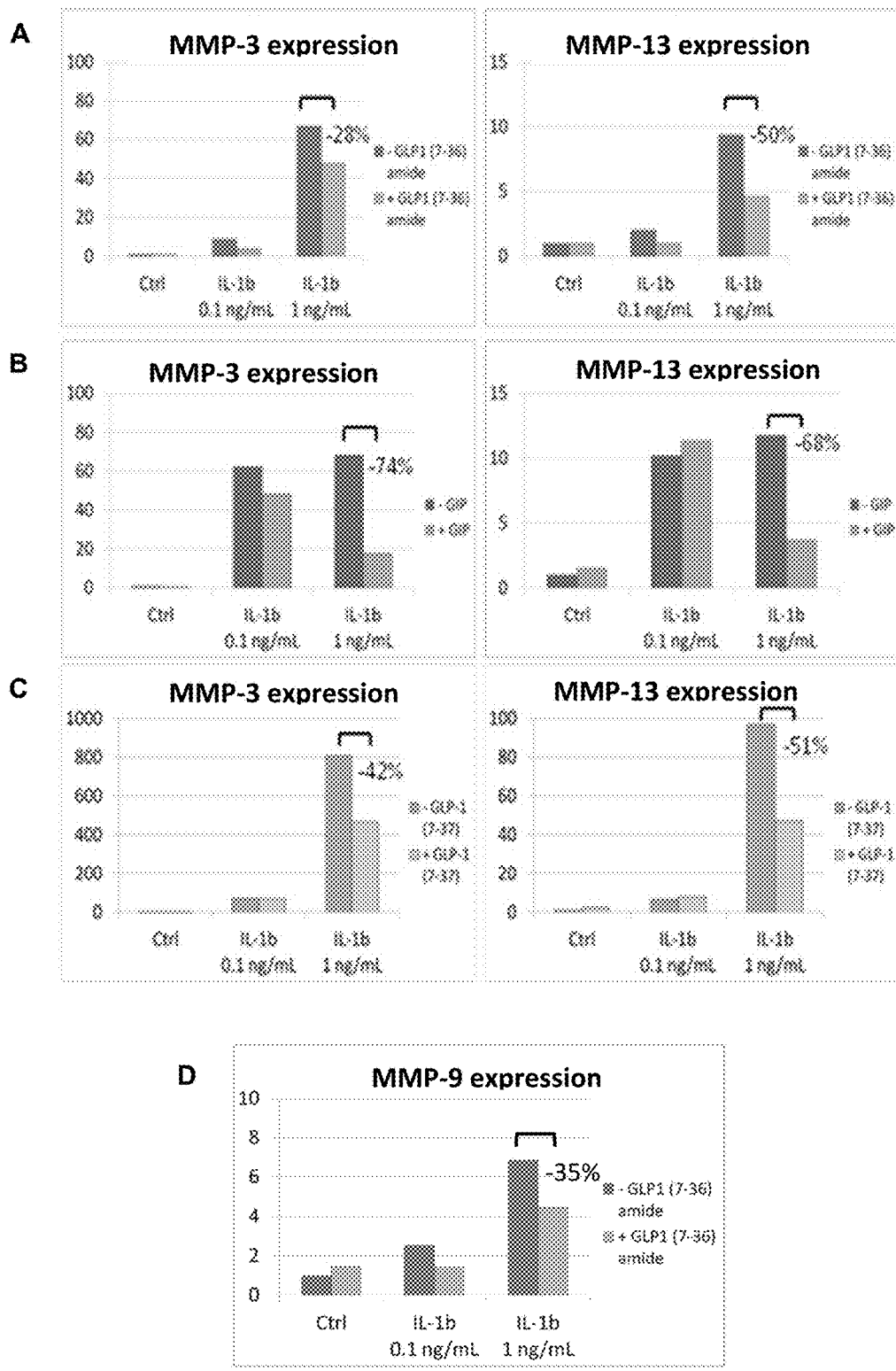
FIG. 2: Effect of the GLP-1 (7-36) amide, GLP-1 (7-37) or GIP peptide on the induction of the expression of the MMP-3, MMP-9 and MMP-13 enzymes in osteoblasts in response to IL-1β (0.1 ng/ml or 1 ng/ml). The values obtained by real-time quantitative RT-PCR are standardized with respect to the values obtained with the control (without IL-1β and without GLP-1 or GIP). A: MMP-3 and MMP-13 expression in the presence or absence of GLP-1 (7-36) amide (10 nM); B: MMP-3 and MMP-13 expression in the presence or absence of GIP (10 nM); C: MMP-3 and MMP-13 expression in the presence or absence of GLP-1 (7-37) (10 nM); D: MMP-9 expression in the presence or absence of GLP-1 (7-36) amide (10 nM).

The incretin hormones GLP-1 (glucagon-like peptide 1) and GIP (gastric inhibitory peptide or glucose-dependent insulinotropic polypeptide) are gut hormones that are released by endocrine cells of the intestinal epithelium in response to the absorption of nutrients. The GLP-1 peptide is produced by the L-cells of the ileum orcolon by proteolytic cleavage of the preproglucagon molecule in the form of an inactive peptide of 37 amino acids. The six N-terminal residues are then cleaved so as to obtain the two active forms present in the blood: GLP-1 (7-37) and the major form GLP-1 (7-36) amide (Vahl et al., 2003). The GIP hormone is a peptide of 42 amino acids that is secreted by the K-cells of the duodenum. Once in the circulation, these hormones are rapidly inactivated by dipeptidyl peptidase IV (DPP-IV) (Deacon et al., 2005; Orskov et al., 1993).

The secretion of incretin hormones is stimulated by glucose, of which they potentiate the effect on insulin-secretin pancreatic β-cells. They therefore have an insulinotropic effect which is observed only in response to an increase in glycaemia (post-prandial glycaemia) (Kreymann et al., 1987). Many studies have also revealed that they increase the mass of pancreatic β-cells and the synthesis of insulin in these cells (Kim et al., 2005; Buteau et al., 2008). The GLP-1 peptide also inhibits the secretion of glucagon, a hyperglycaemic hormone (Heller et al., 1997).

Unlike the GIP peptide, the GLP-1 hormone retains this insulinotropic effect in patients suffering from type 2 diabetes. It is therefore of great therapeutic interest in the treatment of this pathological condition, especially as the insulinotropic effect is glucose-dependent and the risks of hypoglycaemia associated with the administration of GLP-1, even at high doses, are thus limited. GLP-1 analogues resistant to DPP-IV, such as exenatide or liraglutide, have thus been developed and are currently used in the treatment of diabetes.

The incretin hormones also act on the hypothalamus, the gastrointestinal tract and the cardiovascular system (Zhao et al., 2006). In particular, they slow down gastric emptying and help to reduce the amount of food ingested by the individual by contributing to the occurrence of a sensation of satiety (Gutzwiller et al., 1999). The GIP peptide also has specific effects on adipose tissue and appears to improve the use of absorbed lipids (Yip and Wolfe, 2000). It could therefore be envisaged to use these hormones in the treatment of obesity (Neff and Kushner, 2010).

The inventors have presently demonstrated that incretins can have a therapeutic effect in the context of quite another pathological condition: osteoarthritis. They have in fact shown that the presence of GLP-1 (7-37) (SEQ ID NO: 3), GLP-1 (7-36) amide (SEQ ID NO: 4) or GIP (SEQ ID NO: 6) peptide in chondrocyte and osteblast culture media makes it possible to inhibit the overexpression by these cells of several metalloproteases (MMP-3, MMP-9 and MMP-13) in response to a treatment with the cytokine IL-1β which is a major mediator of the arthrotic destruction of cartilage. They have also demonstrated that these peptides inhibit the release of pro-inflammatory prostaglandin E2 (PGE2), another pro-degradative mediator, by chondrocytes in response to IL-1β.

The inventors have thus demonstrated the direct inhibitory action of the incretin hormones GLP-1 and GIP on several factors involved in cartilage destruction in the arthrotic process. The use of these hormones, or analogues thereof, therefore represents a novel strategy for treating osteoarthritis. This strategy is all the more advantageous since several GLP-1 analogues have already proven their innocuousness and have been approved by health authorities.

The present invention therefore relates to a peptide chosen from the group consisting of the GLP-1 peptide, the GIP peptide and analogues of said peptides resistant to dipeptidyl peptidase IV (DPP-IV) for use in the treatment of osteoarthritis.

In the present document, the terms "peptide", "oligopeptide", "polypeptide" and "protein" are used without implied distinction and refer to a chain of amino acids linked by peptide bonds, whatever the number of amino acid residues forming this chain.

According to one embodiment, the peptide used according to the invention is chosen from the group consisting of the GLP-1 peptide and the GIP peptide. The GLP-1 or GIP peptides can be administered in a mature form or in the form of a precursor. The GLP-1 peptide can thus be administered in the form of a protein precursor: preproglucagon (SEQ ID NO: 1) or the precursor GLP-1 (1-37) (SEQ ID NO: 2), or in an active form: the GLP-1 (7-37) peptide (SEQ ID NO: 3) or the GLP-1 (7-36) amide peptide (SEQ ID NO: 4). The GIP peptide can also be administered in the form of its precursor (SEQ ID NO: 5) or in its active form GIP (1-42) (SEQ ID NO: 6). According to one particular embodiment, the peptide used according to the invention comprises, or consists of, a sequence chosen from the group consisting of SEQ ID NOS: 1 to 6. According to one preferred embodiment, the peptide is chosen from the active forms of GLP-1 or GIP, i.e., from the group consisting of the peptides of SEQ ID NO: 3, SEQ ID NO: 4 or SEQ ID NO: 6. Preferably, the peptide is the GLP-1 (7-36) amide peptide (SEQ ID NO: 4).

After administration, the GLP-1 and GIP peptides are rapidly inactivated by the dipeptidyl peptidase IV (DPP-IV) enzyme which cleaves the two N-terminal amino acids. Thus, the half-life time of the GLP-1 or GIP peptide administered intravenously is approximately 2 minutes. These peptides or the precursors thereof are therefore preferably administered continuously, for example by means of a continuous subcutaneous infusion. Thus, according to one particular embodiment, the peptide used according to the invention is a GLP-1 or GIP peptide, or a precursor thereof, preferably a peptide chosen from the group consisting of the GLP-1 (7-37) peptide (SEQ ID NO: 3), the GLP-1 (7-36) amide peptide (SEQ ID NO: 4) and the GIP peptide (SEQ ID NO: 6), more particularly preferably the GLP-1 (7-36) amide peptide (SEQ ID NO: 4), and the peptide is continuously administered to the patient to be treated, preferably by means of a continuous subcutaneous infusion.

According to another embodiment, the peptide is an analogue of the GLP-1 or GIP peptide, preferably an analogue resistant to dipeptidyl peptidase IV (DPP-IV). These analogues, also called incretin mimetics, are GLP-1 receptor or GIP receptor agonists which mimic the action of incretins, but have improved properties compared with the GLP-1 or GIP peptide, such as an increased resistance to DPP-IV and therefore a prolonged circulating half-life time.

The GLP-1 and GIP peptides may be modified in various ways. For example, one or more amino acids of L configuration may be replaced with amino acids of D configuration. The peptide may undergo a post-translational modification and/or an additional chemical modification, in particular a glycosylation, an amidation, an acylation, an acetylation or a methylation. Protective groups may also be added to the C-terminal and/or N-terminal ends. For example, the protective group at the N-terminal end may be an acylation or an acetylation and the protective group at the C-terminal end may be an amidation or an esterification. The peptide of the invention may also comprise pseudopeptide bonds replacing the "conventional" CONH peptide bonds and conferring increased resistance to peptidases, such as $CHOH-CH_2$, $NHCO$, $CH_2-O$, $CH_2CH_2$, $CO-CH_2$, $N-N$, $CH=CH$, $CH_2NH$, and $CH_2-S$. One or more amino acids may also be replaced with rare amino acids, in particular hydroxyproline, hydroxylysine, allohydroxylysine, 6-N-methylysine, N-ethylglycine, N-methylglycine, N-ethyl-asparagine, allo-isoleucine, N-methylisoleucine, N-methylvaline, pyroglutamine and aminobutyric acid, or synthetic amino acids, in particular ornithine, norleucine, norvaline and cyclohexylalanine. The invention also covers the use of the analogues obtained by subjecting the GLP-1 or GIP peptide to conservative substitutions. The term "conservative substitution" as used in this document refers to a substitution of one amino acid residue with another which has similar chemical or physical properties (size, charge or polarity). By way of example, isoleucine, leucine, alanine, valine, phenylalanine, proline and glycine can be mutually conservatively substituted, as can lysine, histidine and arginine; serine, tyrosine and threonine; cysteine and methionine; asparagine, glutamine and tryptophan; or aspartic acid and glutamic acid.

The analogues of the GLP-1 and GIP peptides can have a greater or lesser degree of homology with said peptides. By way of example, liraglutide, which is a GLP-1 analogue, exhibits 97% homology with the human GLP-1 peptide, while exendin-4, another GLP-1 analogue obtained from lizard venom, exhibits only 53% homology. However, preferably, the peptide is an analogue of the GLP-1 or GIP peptide resistant to dipeptidyl peptidase IV (DPP-IV) exhibiting at least 50% homology with the human GLP-1 peptide, and preferably at least 60%, 70%, 80%, 90% or 95% homology with SEQ ID NO: 3 or 4.

Numerous GLP-1 and GIP analogues resistant to DPP-IV have been described and are derived from various strategies intended to improve their resistance and to increase their half-life time in order to reduce the frequency of their administration.

Analogues of the GLP-1 peptide resistant to DPP-IV can in particular be obtained (a) by carrying out selective amino acid substitutions (see, for example, U.S. Pat. No. 5,545,618), for example by substituting the second N-terminal amino acid, which is an L-alanine, with a D-alanine or a serine, (b) by attaching lipophilic substituents to the side chains of the amino acid residues of the GLP-1 peptide (see, for example, European Patent No. 0 944 648), (c) by identifying insulinotropic compounds and testing their human GLP-1 receptor agonist capacity (for example, exendin-3 and -4, initially isolated from lizard venom), (d) by acetylating the GLP-1 peptide or an analogue thereof, as has been done for liraglutide, in which a C-16 palmitoyl group is bonded to a lysine of a modified GLP-1 peptide, (e) by covalently bonding a plasma protein, preferably albumin, to a GLP-1 peptide (for example, albugon (GlaxoSmithKline), CJC-1131 (ConjuChem), CJC-1134, or an exendin-4 analogue covalently bonded to a human albumin (ConjuChem)), (f) by trapping the GLP-1 peptides in biodegradable polymers, or (g) by conjugating the GLP-1 peptide (or an analogue thereof) with a polyethylene glycol (for example, LY315902, LY2199265 or LY2428757 (Eli Lilly)). GLP-1 analogues have been described in numerous patent documents, such as US 2011/0281797, WO 2011/134284 or US 2011/0166321.

The GIP peptide can also be modified in order to increase its resistance to DPP-IV, for example by modifying the N-terminal tyrosine (O'Harte et al., 1999), by substituting the second N-terminal amino acid, which is an L-alanine, with a D-alanine or a serine (Hinke et al., 2002), or by mutating the glutamic acid in position 3 of SEQ ID NO: 6 (Gault et al., 2003) or the alanine in position 13 of SEQ ID NO: 6 (Gault et al., 2003b). A truncated GIP analogue has also been described, the D-Ala$^2$-GIP (1-30) analogue, in which the L-alanine in the second N-terminal position has been substituted with a D-alanine (Widenmaier et al., 2010). Analogues of the GIP peptide exhibiting an increased resistance to DPP-IV have been described in numerous patent documents, such as international patent applications WO 00/58360, WO 98/24464, WO 03/082898 and WO 2010/016944, and also in European Patent No. 0 479 210.

According to one particular embodiment, the peptide used according to the invention is an analogue of the GLP-1 peptide resistant to dipeptidyl peptidase IV, preferably chosen from the group consisting of exenatide (Amylin Pharmaceuticals), exendin-4, liraglutide (Novo Nordisk), albiglutide (or albugon) (GlaxoSmithKline), taspoglutide (Ipsen/Roche), lixisenatide (Sanofi), LY315902 (Eli Lilly), dulaglutide (LY2189265) (Eli Lilly), LY2199265 (Eli Lilly), LY2428757 (Eli Lilly), semaglutide NN9535 (Novo Nordisk), CJC-1131 (ConjuChem), CJC-1134 (ConjuChem) and ZP10 (Aventis/Zealand Pharma). More particularly preferably, the peptide is an analogue chosen from the group consisting of exenatide and liraglutide.

The invention also covers the use of the pharmaceutically acceptable salts of a peptide used according to the invention. The pharmaceutically acceptable salts may be, for example, salts with pharmaceutically acceptable inorganic acids, such as hydrochloric acid, hydrobromic acid, sulphuric acid and phosphoric acid; salts with pharmaceutically acceptable organic acids, such as acetic acid, citric acid, maleic acid, malic acid, succinic acid, ascorbic acid and tartaric acid; salts with pharmaceutically acceptable inorganic bases, such as sodium, potassium, calcium, magnesium or ammonium salts; or salts with organic bases which have a salifiable nitrogen, commonly used in the pharmaceutical art. The methods for preparing these salts are well-known to those skilled in the art.

The peptide according to the invention can be obtained by conventional chemical synthesis (in solid phase or in homogeneous liquid phase) or by enzymatic synthesis. It can also be obtained by means of the method consisting of culturing a host cell comprising a transgene encoding the peptide and expressing said peptide, and extracting said peptide from these host cells or from the culture medium into which the peptide has been secreted.

The peptide used according to the invention can be used alone or in combination with one or more other peptides used according to the invention. The peptides can be administered simultaneously or sequentially.

The peptide used according to the invention can be used as a sole active ingredient or in combination with one or more active substances. The peptide and said active substance(s) can be administered simultaneously or sequentially.

In particular, the peptide can be used in combination with one or more inhibitors of the dipeptidyl peptidase IV enzyme. According to one embodiment, the peptide is used in combination with one or more inhibitors of the dipeptidyl peptidase IV enzyme which are chosen from the group consisting of sitagliptin, saxagliptin, vildagliptin, alogliptin and linagliptin. According to one particular embodiment, the peptide used in combination with one or more inhibitors of the dipeptidyl peptidase IV enzyme is a GLP-1 or GIP peptide, or a precursor thereof, in particular a peptide which comprises, or consists of, a sequence chosen from the group consisting of SEQ ID NOS: 1 to 6. Preferably, the peptide is chosen from the group consisting of the GLP-1 (7-37) peptide (SEQ ID NO: 3), the GLP-1 (7-36) amide peptide (SEQ ID NO: 4) and the GIP peptide (SEQ ID NO: 6), and more particularly preferably the peptide is the GLP-1 (7-36) amide peptide (SEQ ID NO: 4).

The peptide may also be used in combination with one or more substances used in the treatment of osteoarthritis, in particular analgesics such as paracetamol; non-steroidal anti-inflammatories such as acetylsalicylic acid, lysine acetylsalicylate, phenylbutazone, sulindac, diclofenac potassium or sodium, aceclofenac, tiaprofenic acid, ibuprofen, ketoprofen, alminoprofen, fenoprofen, naproxen, flurbiprofen, indomethacin, mefenamic acid, niflumic acid, tenoxicam, meloxicam, piroxicam, and selective cyclooxygenase-2 inhibitors such as celecoxib and etoricoxib; steroidal anti-inflammatories such as betamethasone, dexamethasone, prednisolone, prednisone, tixocortol or triamcinolone; or slow-acting anti-arthritic agents such as drugs comprising chondroitin, chondroitin sulphate (Structum, Chondrosulf), glucosamine or glucosamine sulphate, diacerein (Art 50, Zondar), or unsaponifiable extracts of avocado and soya (piascledine).

The peptide used according to the invention may also be administered in combination with local treatments, such as intra-articular or periarticular corticotherapy, viscosupplementation, or articular lavage; surgical release or prosthetic treatments; or the use of orthoses.

The peptide used according to the invention may also be administered in the form of a nucleic acid encoding said peptide. As used in this document, the term "nucleic acid" is intended to mean any DNA-based or RNA-based molecule. This may involve synthetic or semi-synthetic, recombinant molecules which are optionally amplified or cloned in vectors, and chemically modified, comprising unnatural bases or modified nucleotides comprising, for example, a modified bond, a modified purine or pyrimidine base, or a modified sugar. The nucleic acid may be in the form of single-stranded or double-stranded DNA and/or RNA. According to one preferred embodiment, the nucleic acid is an isolated DNA molecule synthesized by recombinant techniques well-known to those skilled in the art. The nucleic acid may be deduced from the sequence of the peptide used according to the invention and the codon usage may be adjusted according to the host cell in which the nucleic acid must be transcribed. These steps can be carried out according to methods well-known to those skilled in the art, some of which are described in the reference manual Sambrook et al. (2001). Preferably, the carrier used to administer the nucleic acid protects it against any degradation that may harm its effectiveness. Among the carriers that can be used, mention may in particular be made of natural cationic polymers such as chitosan or atelocollagen, or synthetic cationic polymers such as poly(L-lysine), polyethyleneimine (PEI) or dendrimers, which form complexes with nucleic acids; liposomes; cationic liposomes; galactosylated liposomes; liposomes covered with a ligand allowing them to target a cell type, such as immunoliposomes covered with an antibody specific for the target cell (Zheng et al., 2009); liposomes arranged in a nanoparticle formed by polymers (Carmona et al., 2009); or multilayer films of polycations and polyanions.

As used in this document, the term "treatment" or "therapy" refers to any action which makes it possible to reduce, suppress or delay the symptoms associated with a pathological condition. It comprises both a curative treatment and a prophylactic treatment for a disease. A curative treatment is defined by a treatment resulting in a cure or a treatment which relieves, improves and/or eliminates, reduces and/or stabilizes the symptoms of a disease or the suffering that it causes. A prophylactic treatment comprises both a treatment resulting in the prevention of a disease and a treatment which reduces and/or delays the incidence of a disease or the risk of it occurring. In particular, in the context of the present invention, the term "treatment" refers more particularly to the inhibition or the slowing down of the arthrotic destruction of cartilage observed through the pinching of the articular interline on standard x-rays.

The peptide used according to the invention can be used in the treatment of a primary osteoarthritis (without anatomical or traumatic cause) or secondary osteoarthritis. The osteoarthritis treated may affect any joint, in particular the joints of the hip (coxarthrosis), the knee (gonarthrosis), the ankle, the foot, the hand, the wrist, the elbow, the shoulder or the rachis, preferably the joints of the hip, the knee, the hand and the rachis.

The subject to be treated, or patient, is an animal, preferably a mammal. According to one embodiment, the subject to be treated is an animal selected from the group consisting of a dog, a cat, a horse, a cow, a sheep, a pig and a non-human primate. According to one preferred embodiment, the subject to be treated is a human, preferably an adult, and particularly preferably an adult over the age of 50.

According to one particular embodiment, the subject to be treated does not have type II diabetes. Preferably, this patient has a fasting glycaemia of less than 1.26 g/l.

According to another particular embodiment, the subject to be treated is not obese. The body mass index (or BMI, mass/(height)$^2$) makes it possible to estimate the corpulence of a person. According to the WHO classification, a medium corpulence corresponds to a BMI of 18.5 to 25, an overweight person has a BMI of 25 to 30 and an obese person has a BMI greater than 30. Preferably, the subject to be treated has a body mass index of less than 30, more particularly preferably less than 27, and quite particularly preferably less than 25.

According to yet another particular embodiment, the subject to be treated has a fasting glycaemia of less than 1.26 g/l and a body mass index of less than 30, preferably less than 27, and particularly preferably less than 25.

The peptide used according to the invention is administered to the patient in the form of a pharmaceutical composition comprising at least one peptide used according to the invention and a pharmaceutically acceptable support and/or excipient. The peptide used according to the invention may also be administered to the patient in the form of a pharmaceutical composition comprising at least one nucleic acid encoding a peptide used according to the invention and a pharmaceutically acceptable support and/or excipient. The composition may also comprise one or more other active substances as defined above. It may in particular comprise one or more inhibitors of the dipeptidyl peptidase IV enzyme, preferably chosen from the group consisting of sitagliptin, saxagliptin, vildagliptin, alogliptin and linagliptin, or other substances such as analgesics, non-steroidal anti-inflammatories, steroidal anti-inflammatories and slow-acting anti-arthritic agents.

The pharmaceutically acceptable excipients and supports which can be used are well-known to those skilled in the art (Remington's Pharmaceutical Sciences, 18$^{th}$ edition, A. R. Gennaro, published by Mack Publishing Company (1990); Pharmaceutical Formulation Development of Peptides and Proteins, S. Frokjaer and L. Hovgaard, published by Taylor & Francis (2000); and Handbook of Pharmaceutical Excipients, 3$^{rd}$ edition, A. Kibbe, published by Pharmaceutical Press (2000)). The pharmaceutical composition comprising the peptide used according to the invention may be in the form of tablets, capsules, gel capsules, granules, suspensions, emulsions, solutions, polymers, nanoparticles, microspheres, suppositories, enemas, gels, pastes, ointments, creams, patches, potions, injectable compositions, implants, sprays or aerosols. Preferably, the pharmaceutical composition comprising the peptide used according to the invention is in the form of an injectable composition.

The peptide used according to the invention may be administered via any known administration route, including in particular systemically (parenterally, intravenously, etc.), orally, rectally, topically or subcutaneously. According to one preferred embodiment, the peptide used according to the invention is administered orally, subcutaneously or intravenously, preferably subcutaneously or intravenously, and quite particularly preferably subcutaneously. The peptide may also be administered by intra-articular injection, preferably into the arthrotic joint. In this case, it may be administered in combination with other locally acting substances such as hyaluronic acid, or analgesic substances.

The peptide used according to the invention is administered to the patient at a therapeutically effective dose. The term "therapeutically effective dose" as used herein refers to the amount required to observe a therapeutic or preventive activity on the osteoarthritis, in particular the amount required to observe an inhibition or a slowing down of the arthrotic cartilage destruction. The amount of peptide to be administered and the duration of the treatment are evaluated by those skilled in the art according to the physiological condition of the subject to be treated, the nature of the arthrotic joint(s) to be treated, the peptide chosen and the administration route used. The peptide used according to the invention can be administered in the form of a single dose or multiple doses.

According to one embodiment, the peptide is a GLP-1 peptide or a GIP peptide, or a precursor thereof, and is administered continuously, preferably by means of a continuous subcutaneous infusion. According to another embodiment, the peptide is an analogue of the GLP-1 peptide or of the GIP peptide, resistant to DPP-IV as defined above, and is administered by subcutaneous injection once or twice a day. When the peptide is administered in an extended-release pharmaceutical form (for example an extended-release injectable form of exenatide, Bydureon™), the peptide can be administered with a longer separation between administrations, for example once a week.

The peptide, preferably an analogue of the GLP-1 peptide or the GIP peptide, resistant to DPP-IV as defined above, or a nucleic acid encoding said peptide, can also be administered by intra-articular injection, in particular at a rate of one to three injections every three months.

The dose to be administered will depend on the nature of the peptide used, the administration route and the frequency of the administrations.

According to one embodiment, the peptide is administered to the patient in the form of a pharmaceutical composition comprising between 1 µg and 10 mg of peptide per dose unit, preferably orally, subcutaneously or intravenously.

According to one embodiment, the peptide is administered to the patient subcutaneously in the form of an injectable pharmaceutical composition comprising between 5 µg and 5 mg of peptide per dose unit. According to another embodiment, the peptide is administered to the patient subcutaneously in the form of an injectable pharmaceutical composition comprising between 50 ng and 20 µg of peptide per kilo of body weight per dose unit.

The present invention also relates to the use of a peptide chosen from the group consisting of the GLP-1 peptide, the GIP peptide and analogues thereof resistant to dipeptidyl peptidase IV (DPP-IV) for the production of a drug intended for the treatment of osteoarthritis.

The present invention also relates to a method for treating osteoarthritis in a patient, said method comprising the administration to said patient of a therapeutically effective dose of a peptide chosen from the group consisting of the GLP-1 peptide, the GIP peptide and analogues thereof resistant to dipeptidyl peptidase IV (DPP-IV).

All the references mentioned in this description are incorporated into the present application by way of reference.

Other characteristics and advantages of the invention will emerge more clearly on reading the following examples given by way of non-limiting illustration.

EXAMPLES

Materials and Methods

Primary Culture of Chondrocytes

The murine chondrocytes were obtained after enzymatic digestion of femoral heads and knees of 4- to 6-day-old mice. The cells were amplified in a monolayer for 1 week (Gosset et al., 2008).

Primary Culture of Osteoblasts

The murine osteoblasts were obtained after enzymatic digestion of the skulls of 4- to 6-day-old mice. The cells were amplified for 3 weeks, in the presence of ascorbic acid and β-glycerophosphate. The osteoblasts at the end of culture formed a three-dimensional membrane (Sanchez et al., 2009).

Primary Culture Treatments

The cultures were deprived in a serum-free culture medium for 24 h before treatment. The chondrocytes or osteoblasts were then treated with 0.1 or 1 ng/ml of IL-1β for 24 h, in the presence or absence of GLP-1 (7-36) amide (10 nM), GIP (10 nM) or GLP-1 (7-37) (10 nM) (Bachem).

Gene Expression Analysis

The RNAs were extracted using the RNeasy Mini kit (Qiagen) and then reverse-transcribed using the Omniscript kit (Qiagen). The expression level of the genes of interest was quantified by real-time PCR (Light Cycler LC480), relative to the HPRT reference gene, using the following primers:

```
HPRT-antisense:
                            (SEQ ID No: 7)
ATT CAA ATC CCT GAA GTA CTC AT HPRT-sense:
                            (SEQ ID No: 8)
AGG ACC TCT CGA AGT GT GLP1R-antisense:
                            (SEQ ID No: 9)
CAG TCG GCA GCC TAG AGA GT GLP1R- sense:
                            (SEQ ID No: 10)
CTG CCC AGC AAC ACC AGT MMP3-sense:
                            (SEQ ID No: 11)
TG AAA ATG AAG GGT CTT CCG G MMP3-antisense:
                            (SEQ ID No: 12)
GCA GAA GCT CCA TAC CAG CA MMP9-sense:
                            (SEQ ID No: 13)
AAC TAC GGT CGC GTC CAC T MMP9-antisense:
                            (SEQ ID No: 14)
CCA CAG CCA ACT ATG ACC AG MMP13-sense:
                            (SEQ ID No: 15)
TGA TGG CAC TGC TGA CAT CAT MMP13-antisense:
                            (SEQ ID No: 16)
TGT AGC CTT TGG AAC TGC TT
```

Detection of Released MMP-13 by Western Blotting

The amount of MMP-13 produced by the cells was measured by Western blotting (SDS-PAGE and transfer onto a nitrocellulose membrane) using the culture supernatants. The MMP-13 protein was detected with the anti-MMP-13 polyclonal primary antibody (Santa Cruz) and an HRP-coupled secondary antibody. The visualisation was carried out using the Western C kit (Biorad) and the image capture was carried out using the Fujifilm Image Reader device (Fuji).

Detection of Released PGE2 by EIA

The amount of PGE2 produced by the cells was measured by means of the prostaglandin E2 monoclonal EIA kit (Cayman) using the culture supernatants.

Results

Expression of the GLP-1-Specific Receptor

The GLP-1-specific receptor (GLP-1R) is expressed in vitro by the primary murine chondrocytes and osteoblasts. The mRNAs encoding GLP-1R were detected by RT-PCR in the chondrocyte and osteoblast cell lysates at the basal level. These results indicate that chondrocytes, like osteoblasts, express this receptor at their surface, and are therefore potentially sensitive to the effects of ligands of the GLP-1 type.

Inhibition of the Expression of the Prodegradative Enzymes MMP-3, MMP-9 and MMP-13 in the Chondrocytes The addition of GLP-1 (7-36) amide, GIP or GLP-1 (7-37) inhibits the overexpression of the prodegradative enzymes MMP-3, MMP-9 and/or MMP-13 observed in the chondrocytes in response to an IL-1β treatment (FIG. 1). The recombinant peptides alone do not induce the overexpression of the prodegradative enzymes.

Inhibition of the Expression of the Prodegradative Enzymes MMP-3, MMP-9 and MMP-13 in the Osteoblasts The addition of GLP-1 (7-36) amide, GLP-1 (7-37) or GIP inhibits the overexpression of the prodegradative enzymes MMP-3 and MMP-13 observed in the osteoblasts in response to an IL-1β treatment (FIGS. 2A, B and C). The addition of GLP-1 (7-36) amide also inhibits the overexpression of MMP-9 (FIG. 2D). The recombinant peptides alone do not induce the overexpression of the prodegradative enzymes.

Inhibition of Prostaglandin E2 Release by the Chondrocytes

Figure 3:
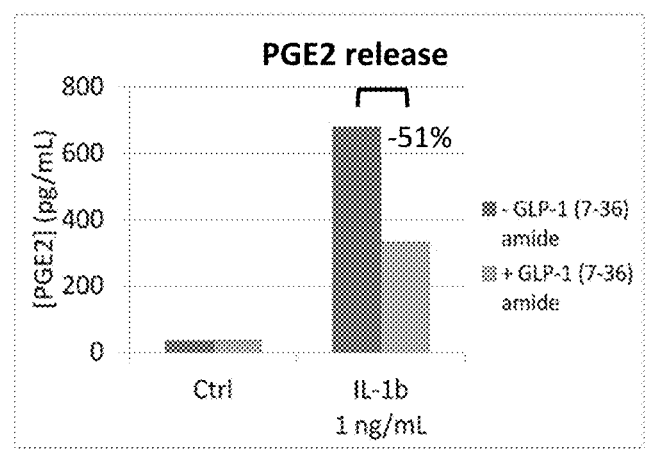
FIG. 3: Effect of the GLP-1 (7-36) amide peptide on the induction of prostaglandin E2 release by chondrocytes in response to IL-1β (1 ng/ml).

The addition of GLP-1 (7-36) amide inhibits the release of prostaglandin E2 (PGE2), a pro-inflammatory lipid mediator, by the chondrocytes, which is observed in response to an IL-1β treatment (FIG. 3). This recombinant peptide alone does not induce PGE2.

LITERATURE REFERENCES

Blanc et al. Osteoarthritis Cartilage 1999; 7: 308-9.
Buteau J. Diabetes Metab 2008; 34 (Suppl. 2):S73-7.
Carmona et al., Mol Pharm. 2009 Jan. 21
Deacon C F. Regul Pept 2005; 128:117-24.
Fosang and Little, 2008, August, Nature Reviews Rheumatology 4, 420-427
Gault, et al, 2003, Biochem. Biophys. Res. Commun., 308:207-213
Gault, et al, 2003b, Cell Biol. International, 27:41-46
Goldring et al. Ann Rheum Dis. 2008; 67 Suppl 3:iii75-82.
Gosset et al. Nat Protoc. 2008; 3(8):1253-60
Gutzwiller et al. Gut 1999; 44:81-6.
Hardy et al. Arthritis Rheum 2002; 46: 1789-1803.
Hashimoto et al. Arthritis Rheum 1998; 41: 1632-8.
Hinke, et al, 2002, Diabetes, 51:656-661
Heller et al. Diabetes 1997; 46:785-91
Kim et al. J Biol Chem 2005; 280:22297-307
Kreymann et al. Lancet 1987; 2:1300-4.
Krzeski et al., Arthritis Res Ther 2007, 9; R109
Little et al. Matrix Biol 2002; 21:271-88.
Miwa et al. Osteoarthritis Cartilage. 2000 January; 8(1):17-24.
Nagase et al. J Biol Chem 1999; 274:21491-4.
Neff and Kushner, Diabetes Metab Syndr Obes. 2010; 3: 263-273
O'Harte, et al, Diabetes. 1999 April; 48(4):758-65.
Orskov et al. Diabetes 1993; 42:658-61.
Rannou et al. Revue du Rhumatisme 2005; 72; 322-330
Sambrook J, Russell D (2001) Molecular cloning: a laboratory manual, Third Edition Cold Spring Harbor
Sanchez et al. Osteoarthritis Cartilage. 2009 April; 17(4): 473-81
Sanchez et al. Arthritis Rheum. 2012 April; 64(4):1193-203.
Sellam and Berenbaum, Nature Reviews Rheumatology 6, 625-635 (November 2010)
Stove et al. Pathobiology 2001; 69:333-8.
Vahl et al. J Clin Endocrinol Metab. 2003 April; 88(4): 1772-9
Widenmaier et al. PLoS ONE 2010; 5(3): e9590
Yip and Wolfe. Life Sci 2000; 66:91-103.
Zheng et al., Blood. 2009 Mar. 19; 113(12):2646-54
Zhao et al. J Pharmacol Exp Ther 2006; 317:1106-13.

The invention claimed is:

1. A method of treating osteoarthritis comprising administering intra-articularly a therapeutically effective dose of a peptide selected from the group consisting of a glucagon-like peptide 1 (GLP-1), a gastric inhibitory peptide (GIP) and analogues thereof resistant to dipeptidyl peptidase IV (DPP-IV) to a subject having osteoarthritis, wherein the therapeutically effective dose of the peptide or the analogue thereof inhibits or slows down the arthritic cartilage destruction.

2. The method according to claim 1, wherein the peptide comprises a sequence selected from the group consisting of SEQ ID NOs: 1 to 6.

3. The method according to claim 2, wherein the peptide is selected from the group consisting of the SEQ ID NO: 4 and SEQ ID NO: 3.

4. The method according to claim 2, wherein the peptide is SEQ ID NO: 6.

5. The method according to claim 1, wherein the peptide is an analogue of the GLP-1 or GIP and is resistant to DPP-IV.

6. The method according to claim 1, wherein the peptide is an analogue of the GLP-1 and is resistant to DPP-IV.

7. The method according to claim 6, wherein the peptide is selected from the group consisting of exenatide, liraglutide, exendin-4, albiglutide, taspoglutide, lixisenatide, dulaglutide (LY2189265), LY315902, LY2199265, LY2428757, semaglutide (NN9535), CJC-1131, CJC-1134 and ZP10.

8. The method according to claim 7, wherein the peptide is selected from the group consisting of exenatide and liraglutide.

9. The method according to claim 1, said method comprising the administration of the peptide selected from the group consisting of the GLP-1, the GIP and the analogues thereof resistant to dipeptidyl peptidase IV (DPP-IV) in combination with one or more other active substances selected from the group consisting of analgesics, non-steroidal anti-inflammatories, steroidal anti-inflammatories and slow-acting anti-arthritic agents.

10. The method according to claim 9, wherein the peptide and said other active substance(s) are administered simultaneously.

11. The method according to claim 9, wherein the peptide and said other active substance(s) are administered sequentially.

12. The method according to claim 1, wherein the peptide is administered in combination with local treatments for osteoarthritis.

13. The method according to claim 1, wherein said method comprises the intra-articular administration of a pharmaceutical composition comprising one or more peptides selected from the group consisting of the GLP-1, the GIP and the analogues thereof resistant to dipeptidyl peptidase IV (DPP-IV) and a pharmaceutically acceptable support and/or excipient.

14. The method according to claim 13, wherein said pharmaceutical composition comprises one or more other active substances selected from the group consisting of analgesics, non-steroidal anti-inflammatories, steroidal anti-inflammatories and slow-acting anti-arthritic agents.

* * * * *